United States Patent
Jang et al.

(10) Patent No.: US 10,117,991 B2
(45) Date of Patent: Nov. 6, 2018

(54) MEDICAL MICRO ROBOT AND MICRO ROBOT SYSTEM HAVING THE SAME

(71) Applicant: INDUSTRY-UNIVERSITY COOPERATION FOUNDATION HANYANG UNIVERSITY, Seoul (KR)

(72) Inventors: Gun Hee Jang, Seoul (KR); Seung Mun Jeon, Seoul (KR)

(73) Assignee: INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 32 days.

(21) Appl. No.: 15/309,265

(22) PCT Filed: Jan. 16, 2015

(86) PCT No.: PCT/KR2015/000479
§ 371 (c)(1),
(2) Date: Nov. 7, 2016

(87) PCT Pub. No.: WO2015/170817
PCT Pub. Date: Nov. 12, 2015

(65) Prior Publication Data
US 2017/0071622 A1    Mar. 16, 2017

(30) Foreign Application Priority Data
May 7, 2014 (KR) .................. 10-2014-0054104

(51) Int. Cl.
*A61M 5/145* (2006.01)
*A61B 17/3207* (2006.01)
(Continued)

(52) U.S. Cl.
CPC ....... *A61M 5/1452* (2013.01); *A61B 17/3207* (2013.01); *A61B 17/320758* (2013.01);
(Continued)

(58) Field of Classification Search
CPC ... A61B 34/30; A61B 2034/303; A61B 34/70; A61B 34/72; A61B 34/73;
(Continued)

(56) References Cited

FOREIGN PATENT DOCUMENTS

KR   10-2009-0122648 A   12/2009
KR   10-2010-0095781 A   9/2010
(Continued)

*Primary Examiner* — Shefali Patel
(74) *Attorney, Agent, or Firm* — Novick, Kim & Lee, PLLC; Sang Ho Lee (57) ABSTRACT

The present invention provides a micro robot including: a drilling body which has a drilling tip formed at an end thereof; a spiral coupling body which has a magnet disposed therein, and is spirally coupled to an outer circumference of the drilling body; and a system control unit which allows the drilling body and the spiral coupling body to spirally move simultaneously or allows the spiral coupling body to spirally move around the drilling body by providing a rotational magnetic field to the magnet. In addition, the present invention also provides a micro robot system including the micro robot.

6 Claims, 5 Drawing Sheets

(51) Int. Cl.
*A61M 31/00* (2006.01)
*A61B 34/30* (2016.01)
*A61B 17/22* (2006.01)
*A61B 90/00* (2016.01)
*A61B 17/00* (2006.01)

(52) U.S. Cl.
CPC ............ *A61B 34/30* (2016.02); *A61M 31/00* (2013.01); *A61B 17/00234* (2013.01); *A61B 17/22* (2013.01); *A61B 90/00* (2016.02); *A61B 2017/00137* (2013.01); *A61B 2017/00345* (2013.01); *A61B 2017/00398* (2013.01); *A61B 2017/00411* (2013.01); *A61B 2017/00893* (2013.01); *A61B 2017/22084* (2013.01); *A61B 2017/22094* (2013.01); *A61B 2034/303* (2016.02)

(58) Field of Classification Search
CPC .......... A61B 2034/731; A61B 17/3207; A61B 17/320758; A61B 2017/00345; A61M 31/00; A61M 37/00; A61M 5/142; A61M 5/145; A61M 5/1452; A61M 2005/14506; A61M 2005/14513

See application file for complete search history.

(56) References Cited

FOREIGN PATENT DOCUMENTS

| | | | | |
|---|---|---|---|---|
| KR | 2011-0033573 | A | 3/2011 | |
| KR | 10-2011-0116968 | A | 10/2011 | |
| KR | 10-1092462 | B1 | 12/2011 | |
| KR | 2011-0139496 | A | 12/2011 | |
| KR | 101092462 | B1 * | 12/2011 | ............... B25J 19/00 |
| WO | WO 2009145405 | A1 * | 12/2009 | ............... A61B 6/03 |

* cited by examiner

MEDICAL MICRO ROBOT AND MICRO ROBOT SYSTEM HAVING THE SAME

CROSS-REFERENCE TO RELATED APPLICATIONS

This application is a national-stage application under 35 U.S.C. § 371 of PCT patent application No. PCT/KR2015/000479, filed Jan. 16, 2015, and claims priority to Korean Patent Application No. 10-2014-0054104, filed on May 7, 2014, in the Korea Intellectual Property Office.

TECHNICAL FIELD

The present invention relates to a medical micro robot, and more particularly, a medical micro robot capable of putting a medicine for dissolving a thrombus into a blood vessel and capable of drilling the thrombus, and a micro robot system having the micro robot.

BACKGROUND ART

In general, a micro robot for a blood vessel treatment may create only mechanical drilling motion in order to treat the blood vessel.

The blood vessel treatment only using the mechanical drilling motion may be relatively easily implemented because an operating method thereof is simple.

However, when treating severe blood vessel diseases such as chronic total occlusion, it is necessary to create relatively high-speed drilling motion, but in this case, there is a great problem in that the high-speed drilling motion may cause secondary damage to a wall of the blood vessel.

As a traditional method for treating blood vessel diseases, there is a surgical procedure in which a medical practitioner manually inserts a catheter through a femoral artery and manipulates the catheter to open the blood vessel.

However, because of structural properties of the catheter, the catheter is difficult to be applied to complicated blood vessels, and the success of the surgical procedure is greatly dictated by the skill of the medical practitioner.

Recently, several advanced research institutes have actively conducted researches regarding micro robots for a blood vessel treatment, as a method for solving the drawback of the catheter.

The micro robot, which has been developed up to now, is mainly used to treat a clogged blood vessel by using mechanical drilling motion.

However, in the case of severe blood vessel diseases such as chronic total occlusion in which the blood vessel is clogged by a hard material, the treatment is difficult to be performed only by the mechanical drilling motion in many instances.

Meanwhile, a thrombolytic agent is a medicine that may biochemically dissolve the thrombus, and the blood vessel disease may be effectively treated when the thrombolytic agent is used together with the mechanical drilling motion.

Therefore, it is necessary to develop a micro robot having both of a mechanical drilling motion function and a medicine delivery function in order to improve blood vessel treatment performance of the micro robot.

As the related art related to the present invention, there is Korean Patent Application Laid-Open No. 10-2009-0122648 (Publication Date: Dec. 1, 2009).

DISCLOSURE

Technical Problem

An object of the present invention is to provide a medical micro robot, which may form a spiral coupling structure, perform forward movement, and drill a thrombus, and may also inject a medicine for dissolving the thrombus, and a micro robot system having the micro robot.

Technical Solution

An exemplary embodiment of the present invention provides a micro robot including: a drilling body which has a drilling tip formed at an end thereof; a spiral coupling body which has a magnet disposed therein, and is spirally coupled to an outer circumference of the drilling body; and a system control unit which allows the drilling body and the spiral coupling body to spirally move simultaneously or allows the spiral coupling body to spirally move around the drilling body by providing rotational magnetic field to the magnet.

A spiral protrusion, which is spirally coupled to the spiral coupling body, may be formed on the outer circumference of the drilling body.

A medicine accommodating space, which has a hollow shape and accommodates a medicine, may be formed in the drilling body.

A medicine injection hole through which the accommodated medicine is injected to the outside may be formed at an end portion of the drilling tip.

The spiral coupling body may include: a piston body which is disposed to be fitted into the medicine accommodating space in order to pump the medicine; and a spiral coil which is formed at an end portion of the piston body and spirally coupled to the spiral protrusion.

A magnet slot into which the magnet is fitted and installed may be formed in the piston body.

The magnet slot may be formed as a cylindrical hole, and the magnet may be formed in a cylindrical bar shape.

The end portion of the piston body may be formed in a convex shape.

A pitch between threads of the spiral protrusion may be larger than a thickness of the spiral coil.

The system control unit may control an operation of a magnetic field generating unit that generates the rotational magnetic field.

A forward movement mode or a rearward movement mode, a medicine injection mode, a drilling mode may be set to the system control unit.

The system control unit 300 may satisfy a condition of $$T^r_{H1} + T^r_{H2} < T^m_{H1} \le \frac{I_{H1} + I_{H2}}{I_{H2}} T^{max,f}_{H1+H2} - \frac{I_{H1}}{I_{H2}} T^r_{H2} + T^r_{H1},$$

when the forward movement and the rearward movement mode is carried out.

When the medicine injection mode is carried out, a condition of $$\frac{I_{H1} + I_{H2}}{I_{H2}} T^{max,f}_{H1+H2} - \frac{I_{H1}}{I_{H2}} T^r_{H2} + T^r_{H1} < T^m_{H1}$$

may be satisfied.

When the drilling mode is carried out, a condition of $T_{H1}{}^r + T_{H2}{}^r < T_{H1}{}^m$ may be satisfied.

Here, $T_{H1}{}^m$ is magnetic torque applied to the drilling body by the rotational magnetic field, $T_{H1+H2}{}^f$ is friction torque generated between the drilling body and the spiral coupling body, $T_{H1}{}^r$ resistance torque generated by the spiral motion of the drilling body, $T_{H2}{}^r$ is resistance torque generated by the spiral motion of the spiral coupling body, $I_{H1}$ is rotational inertia moment of the drilling body, $I_{H2}$ is rotational inertia moment of the spiral coupling body, and $T_{H1+H2}{}^{max\ f}$ is maximum friction torque generated between the drilling body and the spiral coupling body.

In addition, the drilling body and the spiral coupling body may spirally move simultaneously in the forward movement mode and the rearward movement mode.

The spiral coupling body may spirally move in a state in which the spiral coupling body is partially and spirally coupled to the outer circumference of the drilling body and the piston body pumps the medicine accommodated in the medicine accommodating space and discharges the medicine through the medicine injection hole in the medicine injection mode.

The drilling body may spirally move in a state in which the spiral coupling body is completely spirally coupled to the outer circumference of the drilling body in the drilling mode.

Another exemplary embodiment of the present invention provides a micro robot system including the micro robot.

Advantageous Effects

According to the present invention, the spiral coupling structure may be formed, the forward movement may be performed, the thrombus may be drilled, and the medicine for dissolving the thrombus may be injected.

In addition, according to the present invention, the micro robot may be applied to various diseases of the human body in addition to the treatment of the blood vessel, thereby enabling low-priced and high-efficiency treatment with minimum invasion.

BEST MODE

Hereinafter, a medical micro robot of the present invention will be described with reference to the accompanying drawings.

Figure 1:
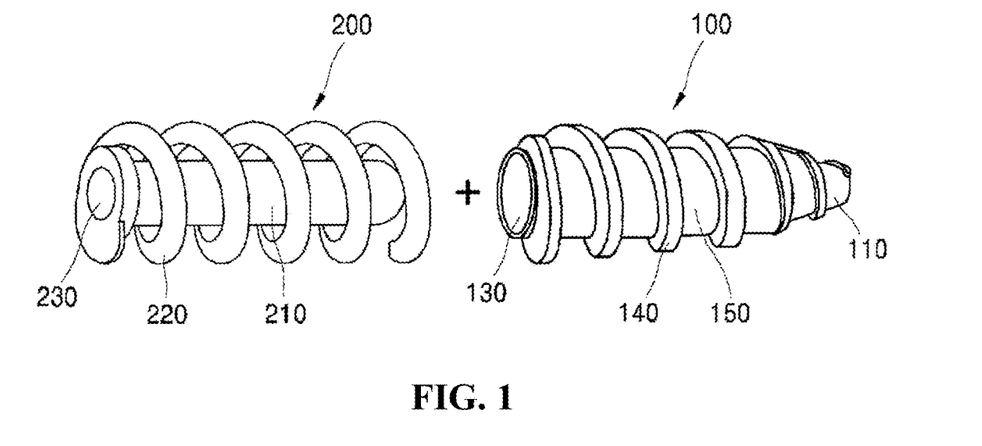
FIG. 1 is a coupled perspective view illustrating a medical micro robot of the present invention.
Figure 2:
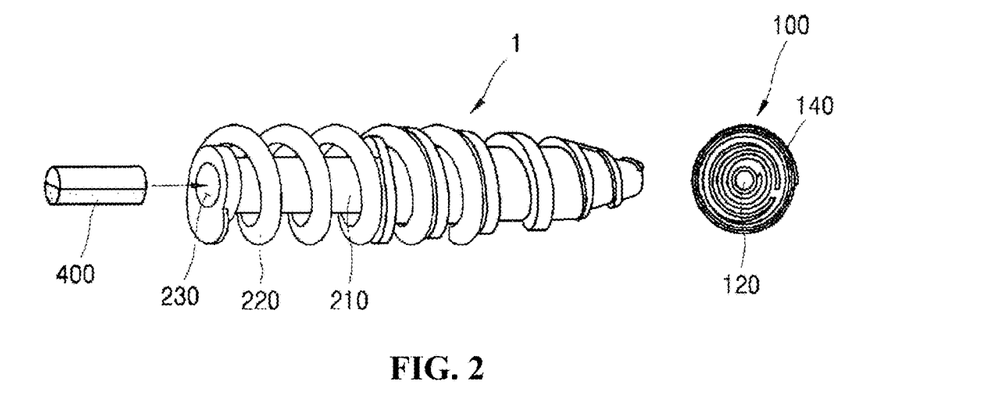
FIG. 2 is an exploded perspective view illustrating the medical micro robot of the present invention.
Figure 3:
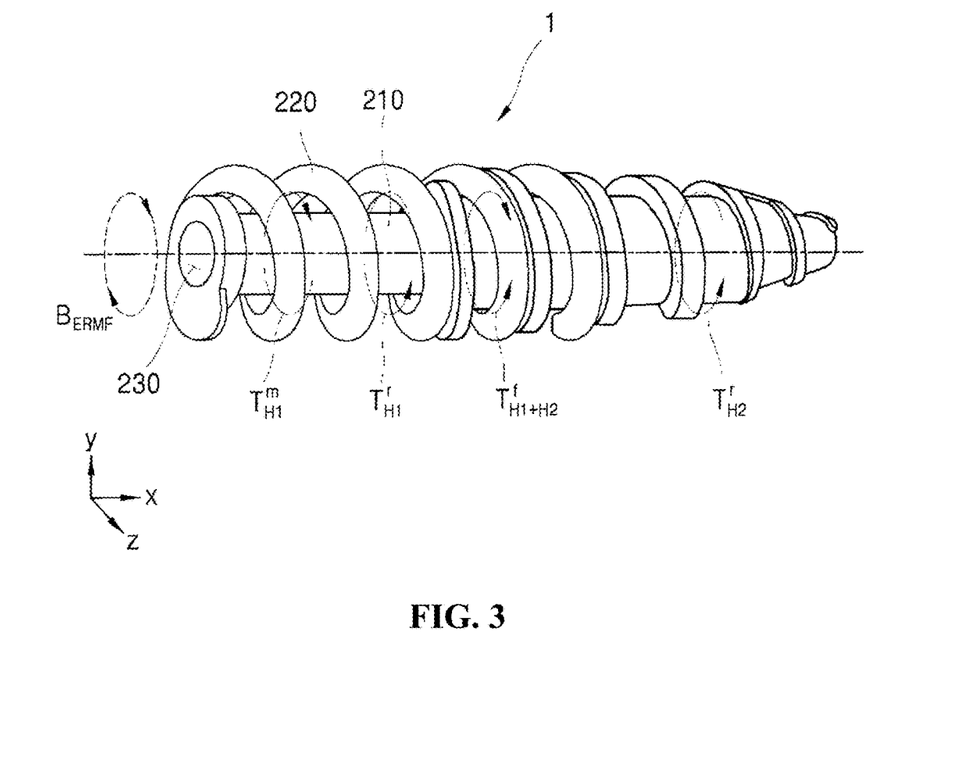
FIG. 3 is a view illustrating torque applied to the medical micro robot of the present invention.

FIG. 1 is a coupled perspective view illustrating a medical micro robot of the present invention, FIG. 2 is an exploded perspective view illustrating the medical micro robot of the present invention, and FIG. 3 is a view illustrating torque applied to the medical micro robot of the present invention.

A configuration of the medical micro robot of the present invention will be described with reference to FIGS. 1 and 2.

A medical micro robot 1 of the present invention broadly includes a drilling body 100, a spiral coupling body 200, a system control unit 300.

The drilling body 100 is formed in a hollow shape, and a diameter at one end or the other end may be gradually decreased.

A drilling tip 110 is formed at the end of the drilling body 100.

The drilling body 100 is formed in a hollow shape, and has a space formed therein.

The space may be a medicine accommodating space 130 that may receive or accommodate a medicine.

The medicine may be a medicine for dissolving the thrombus formed in a blood vessel, or may be a medicine for various purposes.

In addition, the medicine accommodating space 130 provides a space into which a piston body 210 of the spiral coupling body 200, which will be described below, is fitted such that the piston body 210 may be moved leftward and rightward in the medicine accommodating space 130.

Further, a medicine injection hole 120, which exposes the medicine accommodating space 130 to the outside and allows the medicine to be injected to the outside, is formed at the end of the drilling body 100, particularly, at a central portion of the drilling tip 110.

In addition, a spiral protrusion 140, which is formed at a predetermined pitch, protrudes from an outer circumference of the drilling body 100.

The spiral coupling body 200 includes a piston body 210 and a spiral coil 220. An end of the piston body 210 is convexly formed.

The piston body 210 is fitted and disposed into the medicine accommodating space 130 in order to pump the medicine.

One end of the spiral coil 220 is formed to be fixed to the piston body 210, and the spiral coil 220 is formed in a spiral shape having a predetermined pitch along the other end.

The spiral coil 220 may be disposed to be spirally coupled to a spiral groove 150 between threads of the spiral protrusion 140 formed on the outer circumference of the drilling body 100.

Therefore, the spiral coupling body 200 may be spirally coupled to the drilling body 100 so that the spiral coupling body 200 moves forward or rearward at the outer circumference of the drilling body 100 as the spiral coil 220 is spirally coupled to the spiral groove 150 and moved forward or rearward.

In addition, the spiral coupling body 200 has a magnet slot 230.

The magnet slot 230 is formed to have a predetermined depth from one end side of the piston body 210.

The magnet slot 230 may be formed to correspond to a shape of a magnet, and for example, the magnet slot 230 may be formed as a cylindrical groove.

Further, a magnet 400 having a cylindrical bar shape may be fitted, fixed, and installed into the magnet slot 230.

Here, a pitch between the threads of the spiral protrusion 140 may be greater than a thickness of the spiral coil 220.

Referring to FIGS. 2 and 3, a system control unit 300 according to the present invention controls an operation of a magnetic field generating unit (not illustrated) that generates a rotational magnetic field.

With the magnet 400 inserted into the magnet slot 230, the drilling body 100 may create x-axis direction spiral motion by an external rotational magnetic field that rotates in an x-axis direction.

In this case, when the drilling body 100 and the spiral coupling body 200 are partially and spirally coupled to each other, the spiral coupling body 200 and the drilling body 100 are simultaneously rotated by rotational friction torque between the drilling body 100 and the spiral coupling body 200, or the motion, which allows the drilling body 100 and the spiral coupling body 200 to be spirally coupled to each other, may be created.

Magnetic torque applied to the drilling body 100 in the external magnetic field may be expressed by Equation 1.

$$T_{H1}{}^m = m \times B \quad \text{[Expression 1]}$$

Here, $T_{H1}{}^m$ is magnetic torque applied to the drilling body 100 by the external magnetic field, m is magnetic moment of the magnet, and B is intensity of the external magnetic field.

Based on Expression 1, the external rotational magnetic field for creating the spiral motion of the micro robot 1 in the x-axis direction may be expressed by Expression 2.

$$B_{ERMF}(t) = B_0(0, \cos 2\pi ft, \sin 2\pi ft)$$

Here, $B_0$ is intensity of the external rotational magnetic field, f is a frequency of the external rotational magnetic field, and t is time.

The proposed rotational motion equation of the drilling body 100 and the spiral coupling body 200 of the micro robot 1 may be expressed by Expression 3 and Expression 4 as follows.

$$T_{H1}{}^m - T_{H1}{}^r - T_{H1+H2}{}^f = I_{H1}\alpha_{H1} \quad \text{[Expression 3]}$$

$$T_{H1+H2}{}^f - T_{H2}{}^r = I_{H2}\alpha_{H2} \quad \text{[Expression 4]}$$

Here, $T_{H1}{}^m$ is magnetic torque applied to the drilling body 100 by the rotational magnetic field.

$T_{H1}{}^r$ is resistance torque generated by the spiral motion of the drilling body 100.

$T_{H2}{}^r$ is resistance torque generated by the spiral motion of the spiral coupling body 200.

$I_{H1}$ is rotational inertia moment of the drilling body 100, $I_{H2}$ is rotational inertia moment of the spiral coupling body 200, and $T_{H1+H2}{}^{max\,f}$ is maximum friction torque generated between the drilling body 100 and the spiral coupling body 200.

In addition, $\alpha_{H1}$ is an angular acceleration of the drilling body 100, and $\alpha_{H2}$ is an angular acceleration of the spiral coupling body 200.

Referring Expressions 1 to 4, the magnetic torque applied to the drilling body 100 is applied within a range of the following Expression 5, the drilling body 100 and the spiral coupling body 200 simultaneously generates spiral motion by the external rotational magnetic field.

$$T_{H1}^r + T_{H2}^r < T_{H1}^m \le \frac{I_{H1}+I_{H2}}{I_{H2}}T_{H1+H2}^{max,f} - \frac{I_{H1}}{I_{H2}}T_{H2}^r + T_{H1}^r \quad \text{[Expression 5]}$$

Here, $T_{H1+H2}{}^{max\,f}$ is maximum friction torque generated between the drilling body 100 and the spiral coupling body 200.

With the synchronized spiral motion of the drilling body 100 and the spiral coupling body 200, the partially coupled micro robot 1 may accommodate the medicine in the medicine accommodating space 130 and may generate forward thrust without a leak of the medicine, and as a result, the micro robot 1 may effectively create movement and steering motion in a fluid environment such as a blood vessel.

When the magnetic torque applied to the drilling body 100 is applied within a range of the following Expression 6, the drilling body 100 and the spiral coupling body 200 may be spirally coupled.

$$\frac{I_{H1}+I_{H2}}{I_{H2}}T_{H1+H2}^{max,f} - \frac{I_{H1}}{I_{H2}}T_{H2}^r + T_{H1}^r < T_{H1}^m \quad \text{[Expression 6]}$$

The spiral coupling generates pressure in the spiral coupling body 200, and the pressure may allow the medicine accommodated in the medicine accommodating space 130 to be injected to the outside through the medicine injection hole 120.

When the completely spirally coupled micro robot 1 may generate mechanical drilling motion, when the micro robot 1 operates under a condition of Expression 7.

$$T_{H1}^r + T_{H2}^r < T_{H1}^m \quad \text{[Expression 7]}$$

In summary, a forward movement mode or a rearward movement mode, a medicine injection mode, and a drilling mode are preset to the system control unit 300 according to the present invention.

The system control unit 300 satisfies a condition of $$T_{H1}^r + T_{H2}^r < T_{H1}^m \le \frac{I_{H1}+I_{H2}}{I_{H2}}T_{H1+H2}^{max,f} - \frac{I_{H1}}{I_{H2}}T_{H2}^r + T_{H1}^r,$$

when the forward movement and the rearward movement mode is carried out.

When the medicine injection mode is carried out, a condition of $$\frac{I_{H1}+I_{H2}}{I_{H2}}T_{H1+H2}^{max,f} - \frac{I_{H1}}{I_{H2}}T_{H2}^r + T_{H1}^r < T_{H1}^m$$

is satisfied.

When the drilling mode is carried out, a condition of $T_{H1}{}^r + T_{H2}{}^r < T_{H1}{}^m$ is satisfied.

Here, $T_{H1}{}^m$ is magnetic torque applied to the drilling body 100 by the rotational magnetic field.

$T_{H1+H2}{}^f$ is friction torque generated between the drilling body 100 and the spiral coupling body 200.

$T_{H1}{}^r$ is resistance torque generated by the spiral motion of the drilling body 100.

$T_{H2}{}^r$ is resistance torque generated by the spiral motion of the spiral coupling body 200.

$I_{H1}$ is rotational inertia moment of the drilling body 100, 112 is rotational inertia moment of the spiral coupling body 200, and $T_{H1+H2}{}^{max\,f}$ is maximum friction torque generated between the drilling body 100 and the spiral coupling body 200.

In the forward movement mode and the rearward movement mode, the drilling body 100 and the spiral coupling body 200 simultaneously perform the spiral motion.

In the medicine injection mode, the spiral coupling body 200 performs the spiral motion in a state in which the spiral coupling body 200 is partially and spirally coupled to the outer circumference of the drilling body 100, and the piston body 210 pumps the medicine accommodated in the medicine accommodating space 130 so as to inject the medicine to the outside through the medicine injection hole 120.

In the drilling mode, in a state in which the spiral coupling body 200 is spirally coupled to the outer circumference of the drilling body 100, the drilling body 100 performs the spiral motion.

Figure 4:
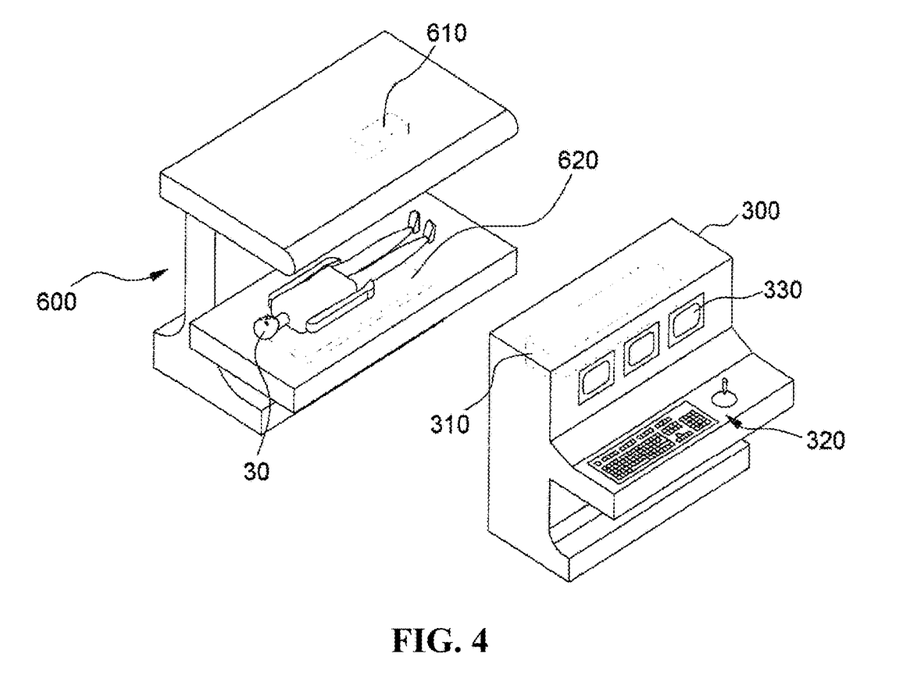
FIG. 4 is a view illustrating a micro robot system having a medical micro robot of the present invention.

FIG. 4 is a view illustrating a system provided with the micro robot of the present invention.

Referring to FIG. 4, the micro robot system of the present invention includes the micro robot 1, a drive unit 600, and the system control unit 300.

Here, the micro robot 1 has the same configuration described with reference to FIGS. 1 to 4, a description will be omitted.

The drive unit 600 transmits driving power to the micro robot 1 inserted into the human body 30 from the outside of a human body 30 which is a test object.

The drive unit 600 includes an external drive unit 610, and driving power generated by the external drive unit 610 includes ultrasonic waves, microwaves or an electromagnetic field.

In particular, the external drive unit 610 may be a magnetic field generating unit that generates the external rotational magnetic field.

In addition, the drive unit 600 further includes a position recognition unit 620 which recognizes a position of the micro robot 1 that moves in the human body 30.

In addition, the position recognition unit 620 may recognize the position of the micro robot 1 by capturing x-ray images of the human body 30.

The system control unit 300 receives position information of the micro robot 1 from the drive unit 600 and controls the drive unit 600.

In addition, the system control unit 300 includes a position control unit 310 that treats ultrasonic position information transmitted from the position recognition unit 610 or treats x-ray images transmitted from the position recognition unit 210.

In addition, the position control unit 310 includes a function of treating the x-ray images and recognizing the position of the micro robot 1.

The system control unit 300 displays the position of the micro robot 1, which is recognized by the position control unit 310, on a display panel 330.

A practitioner controls the drive unit 600 by operating an operating panel 320 of the system control unit 300, and the micro robot 1 may be moved to a position of a lesion.

Next, an experimental example in which a thrombus in a blood vessel is removed and dissolved by using the medical micro robot having the aforementioned configurations will be described.

Figure 5:
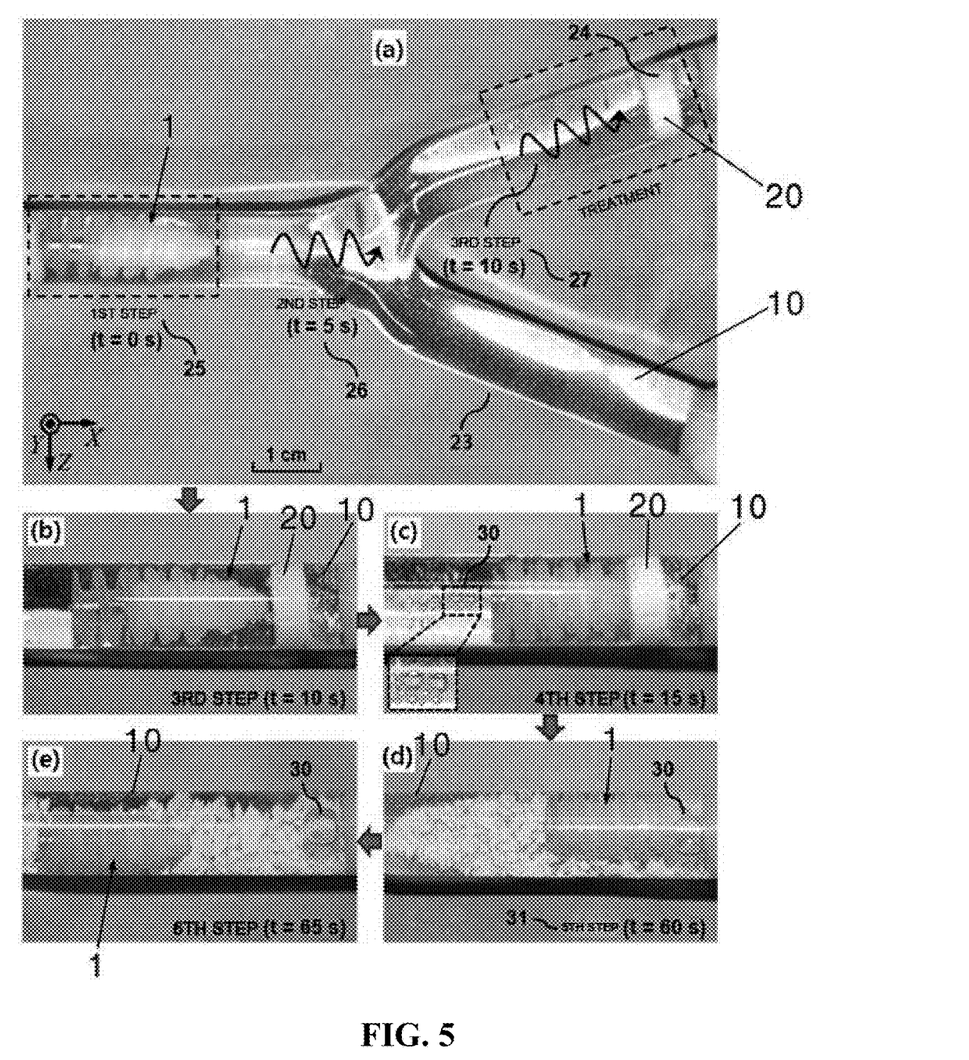
FIG. 5 is experimental photographs illustrating a state in which the medical micro robot of the present invention is positioned in a blood vessel and removes a thrombus.

FIG. 5 is experimental photographs illustrating a state in which the medical micro robot 1 of the present invention is positioned in a blood vessel 10 and removes a thrombus.

FIG. 5(a) illustrates a state in which the micro robot 1 of the present invention moves in the mock blood vessel 10, discharges a medicine, and creates mechanical drilling motion.

First, a mock thrombus 20 including calcium carbonate is installed in the mock blood vessel 10 having a branched tube shape.

An acetic acid, which may chemically react with the calcium carbonate, is accommodated in the micro robot 1. The acetic acid is accommodated or received in the medicine accommodating space 130.

First, the micro robot 1 of the present invention moves forward with the spiral motion by an external rotational magnetic field of 4 mT and 20 Hz which satisfies Expression 5, without discharging the medicine to a treatment area in the mock blood vessel 10.

After the micro robot 1 of the present invention reaches the treatment area, the micro robot 1 cannot move any further because of the mock thrombus 20.

In the micro robot 1 of the present invention, the drilling body 100 and the spiral coupling body 200 are spirally coupled by the external rotational magnetic field of 14 mT and 20 Hz which satisfies Expression 6, and discharge the medicine.

In this case, carbon dioxide bubbles are generated by a chemical reaction between calcium carbonate and carbon dioxide.

With the generation of the carbon dioxide bubbles, it can be confirmed that a thrombolytic agent accommodated in the micro robot 1 actually dissolves the thrombus 20.

The micro robot 1, which is completely spirally coupled after discharging the acetic acid, that is, the medicine, creates effective drilling motion by the external rotational magnetic field of 4 mT and 20 Hz that satisfies Expression 7.

It takes about 45 seconds to complete the drilling motion.

Thereafter, the rearward movement is carried out such that the micro robot returns to an original start position by the external rotational magnetic field of 4 mT and 20 Hz which rotates in a direction opposite to the direction of the external rotational magnetic field used for the forward movement.

In the experimental example in which the micro robot 1 of the present invention is used, it takes about 300 seconds to complete the drilling motion of the micro robot 1 actually filled with water.

Therefore, with the assistance of the thrombolytic agent, the micro robot 1 of the present invention may effectively treat a blood vessel.

With the aforementioned configurations and operations, the exemplary embodiment according to the present invention may form the spiral coupling structure, perform the forward movement, and drill the thrombus, and may also inject the medicine for dissolving the thrombus.

In addition, the exemplary embodiment according to the present invention may be applied to various diseases of the human body in addition to the treatment of the blood vessel, thereby enabling low-priced and high-efficiency treatment with minimum invasion.

While the specific exemplary embodiment related with the medical micro robot of the present invention has been described above, the exemplary embodiments may be modified to various exemplary embodiments without departing from the scope of the present invention.

Therefore, the scope of the present invention should not be limited to the described exemplary embodiment, but should be defined by the appended claims and the equivalents of the claims.

Accordingly, it should be understood that the aforementioned exemplary embodiment is described for illustration in all aspects and is not limited, and the scope of the present disclosure shall be represented by the claims to be described below, instead of the detailed description, and it should be construed that all of the changes or modified forms induced from the meaning and the scope of the claims, and an equivalent concept thereto are included in the scope of the present disclosure.

The invention claimed is:

1. A micro robot comprising:
a drilling body which has a drilling tip formed at an end thereof;
a spiral coupling body which has a magnet disposed therein, and is spirally coupled to an outer circumference of the drilling body; and
a system control unit which allows the drilling body and the spiral coupling body to spirally move simultaneously or allows the spiral coupling body to spirally move around the drilling body by providing a rotational magnetic field to the magnet,
wherein a spiral protrusion, which is spirally coupled to the spiral coupling body, is formed on the outer circumference of the drilling body,
wherein a medicine accommodating space, which has a hollow shape and accommodates a medicine, is formed in the drilling body, and a medicine injection hole through which the accommodated medicine is injected to the outside is formed at an end portion of the drilling tip, and
wherein the spiral coupling body includes:
a piston body which is disposed to be fitted into the medicine accommodating space in order to pump the medicine; and
a spiral coil which is formed at an end portion of the piston body and spirally coupled to the spiral protrusion.

2. The micro robot of claim 1, wherein a magnet slot into which the magnet is fitted and installed is formed in the piston body.

3. The micro robot of claim 2, wherein the magnet slot is formed as a cylindrical hole and the magnet is formed in a cylindrical bar shape.

4. The micro robot of claim 1, wherein the end portion of the piston body is formed in a convex shape.

5. The micro robot of claim 1, wherein the system control unit controls an operation of a magnetic field generating unit that generates the rotational magnetic field, a forward movement mode or a rearward movement mode, a medicine injection mode, and a drilling mode set to the system control unit, the system control unit satisfies a condition of $$T_{H1}^r + T_{H2}^r < T_{H1}^m \le \frac{I_{H1} + I_{H2}}{I_{H2}} T_{H1+H2}^{max,f} - \frac{I_{H1}}{I_{H2}} T_{H2}^r + T_{H1}^r$$

when the forward movement mode and the rearward movement mode are carried out, satisfies a condition of $$\frac{I_{H1} + I_{H2}}{I_{H2}} T_{H1+H2}^{max,f} - \frac{I_{H1}}{I_{H2}} T_{H2}^r + T_{H1}^r < T_{H1}^m$$

when the medicine injection mode is carried out, and satisfies a condition of $T_{H1}^r + T_{H2}^r < T_{H1}^m$ when the drilling mode is carried out, in which the $T_{H1}^m$ is a magnetic torque applied to the drilling body by the rotational magnetic field, the $T_{H1}^r$ is a resistance torque generated by the spiral motion of the drilling body, the $T_{H2}^r$ is a resistance torque generated by the spiral motion of the spiral coupling body, the $I_{H1}$ is a rotational inertia moment of the drilling body, the $I_{H2}$ is a rotational inertia moment of the spiral coupling body, and the $T_{H1+H2}^{max,f}$ is a maximum friction torque generated between the drilling body and the spiral coupling body.

6. The micro robot of claim 5, wherein the drilling body and the spiral coupling body spirally move simultaneously in the forward movement mode and the rearward movement mode, the spiral coupling body spirally moves in a state in which the spiral coupling body is partially and spirally coupled to the outer circumference of the drilling body and the piston body pumps the medicine accommodated in the medicine accommodating space and discharges the medicine through the medicine injection hole in the medicine injection mode, and the drilling body spirally moves in a state in which the spiral coupling body is completely spirally coupled to the outer circumference of the drilling body in the drilling mode.

* * * * *